United States Patent
Kim et al.

(10) Patent No.: US 12,274,705 B2
(45) Date of Patent: Apr. 15, 2025

(54) COMPOSITION COMPRISING CYP4A-INHIBITING COMPOUND AS ACTIVE INGREDIENT FOR PREVENTING OR TREATING METABOLIC DISEASES

(71) Applicant: Korea Basic Science Institute, Daejeon (KR)

(72) Inventors: Gun Hwa Kim, Daejeon (KR); Min Ji Lee, Daejeon (KR); Koon Soon Kim, Daejeon (KR); Hyo Kyun Chung, Daejeon (KR); Ji Hoon Lee, Daejeon (KR); Se Jin Jung, Daejeon (KR); Da Rong Kim, Daejeon (KR)

(73) Assignee: Korea Basic Science Institute, Daejeon (KR)

( * ) Notice: Subject to any disclaimer, the term of this patent is extended or adjusted under 35 U.S.C. 154(b) by 944 days.

(21) Appl. No.: 17/416,883

(22) PCT Filed: Dec. 19, 2019

(86) PCT No.: PCT/KR2019/018147
§ 371 (c)(1),
(2) Date: Jun. 21, 2021

(87) PCT Pub. No.: WO2020/130696
PCT Pub. Date: Jun. 25, 2020

(65) Prior Publication Data
US 2022/0218726 A1 Jul. 14, 2022

(30) Foreign Application Priority Data
Dec. 21, 2018 (KR) .................. 10-2018-0167685

(51) Int. Cl.
*A61K 31/496* (2006.01)
*A61K 31/635* (2006.01)
*A61P 1/16* (2006.01)
*A61P 3/10* (2006.01)

(52) U.S. Cl.
CPC .................................. *A61K 31/635* (2013.01)

(58) Field of Classification Search
CPC ............. A61K 31/496; A61P 1/16; A61P 3/10
See application file for complete search history.

(56) References Cited

U.S. PATENT DOCUMENTS

2009/0163545 A1   6/2009   Goldfarb

FOREIGN PATENT DOCUMENTS

| KR | 1020080099174 A | 11/2008 |
| KR | 1020130017643 A | 2/2013 |
| KR | 101886118 B1 | 9/2018 |

OTHER PUBLICATIONS

International Search Report issued by ISA/KR in connection with PCT/KR2019/018147 on Apr. 3, 2020.
Salahuddin, A., Synthesis and evaluation of 7-chloro-4-(piperazin-1-yl)quinolinesulfonamide as hybrid antiprotozoal agents, Bioorganic & Medicinal Chemistry, 2013, pp. 3080-3089, vol. 21, No. 11, Elsevier.

*Primary Examiner* — Bruck Kifle
(74) *Attorney, Agent, or Firm* — Levenfeld Pearlstein, LLC (57) ABSTRACT

The present invention relates to a composition comprising a CYP4A-inhibiting compound as an active ingredient for preventing or treating metabolic diseases, more specifically to a composition comprising the compound expressed by chemical formula 1 of the present invention or pharmaceutically acceptable salt thereof as an active ingredient for preventing, ameliorating or treating metabolic diseases.

8 Claims, 7 Drawing Sheets

COMPOSITION COMPRISING CYP4A-INHIBITING COMPOUND AS ACTIVE INGREDIENT FOR PREVENTING OR TREATING METABOLIC DISEASES

TECHNICAL FIELD

This application claims priority to Korean Patent Application No. 10-2018-0167685 filed on Dec. 21, 2018, and the entire specifications of which are incorporated herein by reference in their entireties.

The present invention relates to a composition comprising a CYP4A-inhibiting compound as an active ingredient for preventing or treating metabolic diseases, more specifically to a composition comprising the compound expressed by chemical formula 1 of the present invention or pharmaceutically acceptable salt thereof as an active ingredient for preventing, ameliorating or treating metabolic diseases.

BACKGROUND OF THE INVENTION

As the visceral fat-type obesity of modern people increases due to the change of living environment, the incidence of diseases such as diabetes, insulin resistance syndrome, fatty liver, lipid metabolism abnormality (hyperlipidemia), and high blood pressure is rapidly increasing. These diseases are classified as metabolic diseases (metabolic syndrome). These diseases, independently of each therapeutic mechanism, increase the risk of mutual occurrence and are associated with multiple biological metabolic changes such as aging, stress and decreased immune function.

First, diabetes is a major factor in morbidity and mortality. Chronically elevated blood sugar levels cause debilitating complications, such as: nephropathy, often requiring dialysis or a kidney transplant; peripheral neuropathy; retinopathy leading to blindness; ulcers in the legs and feet resulting in amputation; fatty liver disease that sometimes develops into cirrhosis; and virulence for coronary artery disease and myocardial infarction.

There are two main types of diabetes. Type I, or insulin-dependent diabetes mellitus (IDDM), is caused by autoimmune destruction of insulin-producing beta cells of the pancreatic islets. The disease usually develops in infancy or puberty. Treatment for the above disease mainly consists of injecting insulin several times a day, at which time, the blood sugar level is checked several times to control the insulin dose, because excessive insulin causes hypoglycemia and damage to the brain or other functions.

Type II (Type 2), or non-insulin-dependent diabetes mellitus (NIDDM) typically develops in adults. NIDDM is associated with the resistance of glucose-utilizing tissues such as adipose tissue, muscle and liver to the action of insulin. Initially, pancreatic islet beta cells compensate by secreting excess insulin. Ultimate pancreatic islet failure results in decompensation and chronic hyperglycemia. Conversely, moderate islet insufficiency precedes or coincides with peripheral insulin resistance. There are several groups of medications useful for the treatment of NIDDM: 1) insulin-releasing agents that directly stimulate insulin secretion but have the risk of causing hypoglycemia; 2) Meal insulin-releasing agents that enhance glucose-induced insulin secretion but must be taken before each meal; 3) biguaniads, including metformin, which inhibit hepatic gluconeogenesis (which is greatly elevated in diabetes); 4) Insulin sensitizers such as ciglitazone and pioglitazone as a thiazolidinedione derivative that improves peripheral responsiveness to insulin but has side effects such as weight gain, edema and hepatotoxicity; 5) Insulin injection, often required at the end of NIDDM when islets fail under chronic hyperstimulation.

Insulin resistance also occurs without significant hyperglycemia and is commonly associated with atherosclerosis, obesity, hyperlipidemia and essential hypertension. Although the underlying mechanism of insulin resistance is unclear, it has been proposed that endoplasmic reticulum (ER) stress is a novel mechanism for the development of insulin resistance in obese individuals. ER stress has been reported to be caused by disruption of $Ca^{2+}$ homeostasis, overload of protein/lipid biosynthesis, and oxidative stress, and recently ER stress and UPR pathways have been shown to play a role in the pathogenesis of diabetes. However, the precise mechanisms directly regulating the UPR pathway are not well understood.

Insulin resistance is also associated with fatty liver, which can develop into chronic inflammation (NASH: "nonalcoholic steatohepatitis"), fibrosis and cirrhosis.

On the other hand, as described above, since nonalcoholic fatty liver disease (non-alcoholic fatty liver disease (NAFLD)/fatty liver, steatohepatitis, steatohepatitis-related (associated) cirrhosis, etc.) occurring due to insulin resistance, diabetes, etc. has been reported in many cases, the treatment mechanisms and strategies of the above diseases may be fundamentally similar, but, substantially, depending on specific therapeutic substances, it is controversial how much effective level of therapeutic efficacy can be shown for liver diseases such as steatohepatitis, apart from the effect of reducing insulin resistance. So far, there is no drug approved for the treatment of nonalcoholic fatty liver disease. A treatment for steatohepatitis or nonalcoholic fatty liver-associated cirrhosis is absolutely necessary. However, to date, there are no effective and safe approved drugs for ameliorating fibrosis. Currently, many studies are being conducted, and some effects are observed, but there are still limitations in clinical application. For example, in the case of metformin used for the treatment of type 2 diabetes, it was reported that there was no histological improvement effect of steatohepatitis in studies of adult and pediatric NASH (nonalcoholic steatohepatitis) patients (Non-Patent Literature 1, Non-Patent Literature 2). It was also reported that the administration of pioglitazone did not improve liver fibrosis (Non-Patent Literature 3).

Therefore, there is a demand for the development of therapeutic agents that show effective effects in various ways for metabolic diseases such as diabetes and fatty liver disease.

PRIOR ART LITERATURE

Non-Patent Literature (Non-patent literature 1) Cheon G J, Kim Y D, Pharmacological treatment of nonalcoholic fatty liver disease: limitations, Korean Society of Internal Medicine, Spring Conference Papers 2018, 251-256.

(Non-patent literature 2) Haukeland J W et al., Metformin in patients with nonalcoholic fatty liver disease: a randomized, controlled trial. Scand J Gastroenterol 2009; 44:853-860.

(Non-patent literature 3) Arun J. Sanyal et al., Pioglitazone, Vitamin E, or Placebo for Nonalcoholic Steatohepatitis, N Engl J Med 2010; 362:1675-1685.

DETAILED DESCRIPTION OF THE INVENTION

Technical Problem

Accordingly, the present inventors have made diligent efforts to find a substance that exhibits excellent efficacy against metabolic diseases of disease groups such as diabetes and fatty liver disease, as a result, the present invention has been confirmed and completed that the compounds of Formula 1 disclosed in the present invention have a remarkable CYP4A inhibitory effect and promote glucose uptake into hepatocytes, not only inhibits fat accumulation in liver cells and inhibits the production of reactive oxygen species due to ER stress, but also exhibits a therapeutic effect on steatohepatitis.

Accordingly, an object of the present invention is to provide a pharmaceutical composition for preventing or treating metabolic diseases, comprising a compound of Formula 1 or a pharmaceutically acceptable salt thereof as an active ingredient.

It is also an object of the present invention to provide a pharmaceutical composition for preventing or treating metabolic diseases, consisting of a compound of Formula 1 or a pharmaceutically acceptable salt thereof as an active ingredient.

It is also an object of the present invention to provide a pharmaceutical composition for preventing or treating metabolic diseases, consisting essentially of a compound of Formula 1 or a pharmaceutically acceptable salt thereof as an active ingredient:

<Formula 1> wherein R1, R2, R3, R4, R5 and R6 are each independently selected from the group consisting of hydrogen, halo, hydroxy, amino, carboxyl, cyano, nitro, alkyl, alkenyl, alkynyl and alkoxy.

Another object of the present invention is to provide a food composition for preventing or improving metabolic diseases, comprising the compound of Formula 1 or a pharmaceutically acceptable salt thereof as an active ingredient.

In addition, it is to provide a food composition for the prevention or improvement of metabolic diseases, consisting of the compound of Formula 1 or a pharmaceutically acceptable salt thereof as an active ingredient.

In addition, it is to provide a food composition for the prevention or improvement of metabolic diseases, consisting essentially of the compound of Formula 1 or a pharmaceutically acceptable salt thereof as an active ingredient.

Another object of the present invention is to provide the use of the compound of Formula 1 or a pharmaceutically acceptable salt thereof for preparing an agent for the prevention or treatment of metabolic diseases.

Another object of the present invention is to provide a method for treating a metabolic disease comprising administering to a subject in need thereof an effective amount of a composition comprising the compound of Formula 1 or a pharmaceutically acceptable salt thereof as an active ingredient.

Technical Solution

In order to achieve the above object of the present invention, the present invention It provides a composition for preventing, improving or treating metabolic diseases, comprising the compound of Formula 1 or a pharmaceutically acceptable salt thereof as an active ingredient.

In addition, the present invention provides a composition for preventing, improving or treating metabolic diseases, consisting of the compound of Formula 1 or a pharmaceutically acceptable salt thereof as an active ingredient.

In addition, the present invention provides a composition for the prevention, improvement or treatment of metabolic diseases, consisting essentially of a compound of Formula 1 or a pharmaceutically acceptable salt thereof as an active ingredient:

<Formula 1> wherein R1, R2, R3, R4, R5 and R6 are each independently selected from the group consisting of hydrogen, halo, hydroxy, amino, carboxyl, cyano, nitro, alkyl, alkenyl, alkynyl and alkoxy.

In order to achieve the other object of the present invention, the present invention provides the use of the compound of Formula 1 or a pharmaceutically acceptable salt thereof for preparing an agent for the prevention or treatment of metabolic diseases.

In order to achieve another object of the present invention, the present invention the method of treating a metabolic disease comprising administering to a subject in need thereof an effective amount of a composition comprising the compound of Formula 1 or a pharmaceutically acceptable salt thereof as an active ingredient.

Hereinafter, the present invention will be described in more detail.

The following terms in the present invention have the meanings set forth below unless otherwise indicated. Any terms not defined have the meanings understood in the art.

In the present invention, the term 'halo' or 'halogen' refers to fluorine (F), chlorine (Cl), bromine (Br), and iodine (I).

In the present invention, the term 'cyano' group means —CN.

In the present invention, the term 'amino', alone or in combination, may mean a primary, secondary or tertiary amino group bonded through a nitrogen atom. In the present invention, the secondary amino group may mean having an alkyl substituent, and the tertiary amino group may mean having two similar or different alkyl substituents. Although not limited thereto, it may be, for example, —NH$_2$, methylamino, ethylamino, dimethylamino, diethylamino, or methyl-ethylamino. Preferably, it may be one selected from the group consisting of primary amino and C1-C6 alkylamino (more preferably C1-C4 alkylamino, even more preferably C1-C3 alkylamino), and alkyl is understood by reference to the description that follows.

In the present invention, the term 'alkylamino' is understood to have the same meaning as 'aminoalkyl'. Here, there may be one or two or more alkyl groups attached to the amino group.

In the present invention, the term 'nitro' group means —NO$_2$.

In the present invention, unless otherwise specified, the term 'substituted' means that at least one substituent, for example, includes one or two or more halogen atom, nitro, hydroxy, cyano, amino, thiol, carboxyl, amide, nitrile, sulfide, disulfide, sulfenyl, formyl, formyloxy or formylamino. Unless otherwise specified, when the structure obtained by such substitution does not significantly adversely affect the properties of the compound represented by the formula 1 of the present invention (especially activity related to the intended use in the present invention), any group or structure described for the compound represented by formula 1 of the present invention may be substituted.

The term 'alkyl' refers to a monovalent group formed by the loss of one hydrogen atom in an aliphatic saturated hydrocarbon. In the present invention, the alkyl may preferably mean an unsubstituted or substituted linear (straight-chain) or branched (including branched-chain) alkyl type having 1 to 6 carbon atoms (C1, C2, C3, C4, C5 or C6). C1-C6 linear or branched alkyl includes, but is not limited to, methyl, ethyl, n-propyl, isopropyl, n-butyl, sec-butyl, tert-butyl, n-pentyl, isopentyl, neo pentyl, tert-pentyl, n-hexyl, isohexyl, and the like. More preferably, alkyl in the present invention may be unsubstituted or substituted C1-C4 linear or branched alkyl, and even more preferably unsubstituted or substituted C1-C3 linear or branched alkyl.

The term 'alkenyl' refers to an aliphatic unsaturated hydrocarbon group having at least one (ie, one or more) double bonds. In the present invention, alkenyl may preferably mean an unsubstituted or substituted linear or branched alkenyl type having 1 to 6 carbon atoms (01, C2, C3, C4, C5 or C6). C1-C6 linear or branched alkenyl can be, for example, but not limited to, vinyl (—CH=CH$_2$), allyl (—CH$_2$CH=CH$_2$), —CH=CH(CH$_3$), —CH=C(CH$_3$))$_2$, —C(CH$_3$)=CH$_2$, —C(CH$_3$)=CH(CH$_3$), —C(CH$_2$CH$_3$)=CH$_2$, 1,3-butadienyl (—CH=CH—CH=CH$_2$) and hepta-1,6-dien-4-yl (—CH$_2$—(CH$_2$CH=CH$_2$)$_2$) and the like. More preferably, alkenyl in the present invention may be unsubstituted or substituted C1-C4 linear or branched alkenyl, and even more preferably unsubstituted or substituted C1-C3 linear or branched alkenyl.

The term 'alkynyl' refers to an aliphatic unsaturated hydrocarbon group having at least one (ie, one or more) triple bonds. In the present invention, the alkynyl may preferably mean an unsubstituted or substituted linear or branched alkynyl type having 1 to 6 carbon atoms (C1, C2, C3, C4, C5 or C6). C1-C6 linear or branched alkynyl includes, but is not limited to, for example, ethynyl (—C≡CH), —C≡CH(CH$_3$), —C≡(CH$_2$CH$_3$), —CH$_2$C≡CH, —CH$_2$C≡C(CH$_3$) and —CH$_2$C≡C(CH$_2$CH$_3$) and the like. More preferably, alkynyl in the present invention may be unsubstituted or substituted C1-C4 linear or branched alkynyl, and even more preferably unsubstituted or substituted C1-C3 linear or branched alkynyl.

The term 'alkoxy' means '-O-alkyl group', and alkyl is as described above.

In the present invention, alkoxy may preferably mean an unsubstituted or substituted linear or branched alkoxy substituent type having 1 to 6 carbon atoms (C1, C2, C3, C4, C5 or C6). C1-C6 linear or branched alkoxy includes, but is not limited to, for example, methoxy, trifluoromethoxy, ethoxy, n-propoxy, isopropoxy, n-butoxy, t-butoxy, sec-butoxy, n-pentoxy and the like. More preferably, alkoxy in the present invention may be unsubstituted or substituted C1-C4 linear or branched alkoxy, and even more preferably unsubstituted or substituted C1-C3 linear or branched alkoxy.

In one embodiment, preferably, the present invention provides a composition for preventing, improving or treating metabolic diseases, comprising the compound of Formula 1 or a pharmaceutically acceptable salt thereof as an active ingredient:

<Formula 1>

In the Formula 1, wherein R1, R2, R3, R4, R5 and R6 in the compound are each independently selected from the group consisting of hydrogen; halo; hydroxy; amino; carboxyl; cyano; nitro; unsubstituted or substituted C1-C6 linear or branched alkyl; unsubstituted or substituted C1-C6 linear or branched alkenyl; unsubstituted or substituted C1-C6 linear or branched alkynyl; and unsubstituted or substituted C1-C6 linear or branched alkoxy.

As another embodiment, preferably, the compound of Formula 1 included in the composition of the present invention, R1, R2, R4, R5 and R6 are hydrogen, R3 is selected from the group consisting of halo; hydroxy; amino; carboxyl; cyano; nitro; unsubstituted or substituted C1-C6 linear or branched alkyl; unsubstituted or substituted C1-C6 linear or branched alkenyl; unsubstituted or substituted C1-C6 linear or branched alkynyl; and unsubstituted or substituted C1-C6 linear or branched alkoxy.

In this embodiment, most preferably, the compound included in the composition of the present invention may be (N-(4-((4-(7-chloroquinolin-4-yl)piperazin-1-yl)sulfonyl) phenyl)acetamide), it specifically has a structure of the following Formula 1-1 (it may be referred to as #18-1 herein).

<Formula 1-1>

As another embodiment, preferably, the compound of Formula 1 included in the composition of the present invention, R1, R2, R3, R4 and R6 are hydrogen, R5 is selected from the group consisting of halo; hydroxy; amino; carboxyl; cyano; nitro; unsubstituted or substituted C1-C6 linear or branched alkyl; unsubstituted or substituted C1-C6 linear or branched alkenyl; unsubstituted or substituted C1-C6 linear or branched alkynyl; and unsubstituted or substituted C1-C6 linear or branched alkoxy.

In this embodiment, most preferably, the compound included in the composition of the present invention may be (N-(4-((4-(2-methylquinolin-4-yl)piperazin-1-yl)sulfonyl) phenyl)acetamide), it specifically has a structure of the following Formula 1-2 (it may be referred to as #18-2 herein).

<Formula 1-2>

The compounds may be prepared by chemical synthesis methods known in the art, or may be commercially purchased and used.

In the present invention, the term 'pharmaceutically acceptable' means that it is useful for preparing a generally safe, non-toxic, and biologically desirable pharmaceutical composition, and is useful not only for veterinary use but also for human pharmaceutical use.

In the present invention, the pharmaceutically acceptable salt means a salt of the compound represented by Formula 1 (in particular, the most preferred example is a compound of Formula 1-1 or Formula 1-2), which is pharmaceutically acceptable and has a desired pharmacological activity as defined above. Examples of such salts include, but are not limited to, acid addition salts formed with inorganic acids (e.g., hydrochloric acid, hydrobromic acid, sulfuric acid, phosphoric acid, nitric acid, etc.).], and salts formed with organic acids such as acetic acid, oxalic acid, tartan acid, succinic acid, malic acid, fumaric acid, maleic acid, ascorbic acid, benzoic acid, tannic acid, pamoic acid, alginic acid, polyglutamic acid, naphthalene sulfonic acid, naphthalene naphthalene disulfonic acid, and poly-galacturonic acid. The compounds may also be administered in the form of pharmaceutically acceptable quaternary salts known to those skilled in the art, in particular chloride, bromide, iodide, —O-alkyl, toluenesulfonate, methylsulfonate, sulfonate, phosphate, or carboxylates (e.g., benzoates, succinates, acetates, glycorates, maleates, malates, fumarates, citrates, tartrates, ascorbates, cinnamoates, mandelo ate and diphenylacetate) are included. In the present invention, the compounds may be provided in any form, including all salts, hydrates and solvates that can be prepared by conventional methods, as well as in the form of pharmaceutically acceptable salts thereof.

The present inventors were confirmed that the compound represented by Formula 1 (in particular, the most preferred example is a compound of Formula 1-1 or Formula 1-2) not only has an excellent inhibitory effect on CYP4A than HET0016 (N-hydroxy-N'-(4-butyl-2-methylphenyl)-formamidine), which is conventionally known as a cytochrome P450 4A (CYP4A)-specific inhibitor, but also remarkably, it can exhibit preventive and therapeutic effects on metabolic diseases of diabetes and fatty liver disease (especially NAFLD).

Specifically, the present inventors confirmed that inhibition of cytochrome P450 4A (CYP4A) is a potent therapeutic target for hepatic insulin resistance and apoptosis induced by ER stress through previous studies (Korea Patent 10-1235811). In the mammalian liver, the cytochrome P450 enzyme family (CYP450s) is mainly localized in the ER membrane. The present inventors have been confirmed that CYP4A inhibitors suppress the stress of the endoplasmic reticulum, decrease the level of insulin in the blood, show a mechanism for inhibiting apoptosis of liver cells through the preceding studies, so it can be used as a pharmaceutical composition for preventing or treating obesity-derived diabetes and fatty liver.

In the present invention, the treatment may mean, unless otherwise stated, reversing, alleviating, inhibiting the progression of, or preventing the disease or condition to which the term applies, or one or more symptoms of the disease or condition.

Metabolic disease (or metabolic syndrome) refers to a group of diseases in which various metabolic abnormalities occur in combination, including obesity, type 2 diabetes caused by insulin resistance, and risk factors for various metabolic-related cardiovascular diseases. This is a useful concept that can encompass and explain insulin resistance and its related complex and various metabolic abnormalities and clinical features. In the present invention, it refers to a disease or syndrome in which risk factors such as obesity, diabetes, fatty liver disease, etc. increase together.

In the present invention, the term 'metabolic disease' may include, but is not limited to, diabetes or fatty liver disease.

In the present invention, "diabetes" is a chronic disease characterized by abnormal glucose metabolism. The diabetes is either a result of an absolute deficiency in the production of insulin, the most important hormone that regulates blood glucose levels (insulin-dependent diabetes mellitus or type 1 diabetes), or is caused by a result of a decrease in the action of insulin in a target organ (non-insulin-dependent diabetes mellitus) or type 2 diabetes).

Preferably, diabetes in the present invention refers to non-insulin-dependent diabetes mellitus (type 2 diabetes). The non-insulin-dependent diabetes mellitus generally exhibits abnormalities in glucose metabolism and lipid metabolism. That is, in the case of the non-insulin-dependent diabetes mellitus, insulin secretion is delayed or a sufficient amount is not secreted after food intake, so glucose production in the liver does not decrease, and the utilization of blood sugar by peripheral tissues such as muscle, liver, and fat does not increase. The postprandial hyperglycemia caused by this always stimulates insulin secretion, resulting in chronic hyperinsulinemia. If this condition continues, the beta cells can no longer maintain the increased rate of insulin secretion, ultimately resulting in insulin resistance. Persistent insulin resistance leads to problems with insulin production, leading to hypoinsulinemia. In particular, a decrease in the ratio of insulin to glucagon increases hepatic gluconeogenesis.

In addition, an increase in blood free fatty acids has been suggested as a cause of insulin resistance. An increase in free fatty acids in the blood increases the blood glucose level by inhibiting glucose utilization by insulin in peripheral tissues and interfering with gluconeogenesis in liver tissues. In the non-insulin-dependent diabetes mellitus, not only an increase in free fatty acids in the blood but also an increase in blood cholesterol and triglycerides and a decrease in HDL-cholesterol appear. The incidence of such dyslipidemia is 2 to 4 times higher than that of normal people.

Meanwhile, studies related to diabetes and diabetic complications have reported that diabetes is closely related to oxidative stress. Chronic hyperglycemia seen in diabetes increases the production of free radicals by various pathways such as auto-oxidation of glucose and protein glycation, and oxidative stress is increased by these highly reactive substances. Moreover, the expression and activity of antioxidant enzymes are insufficient to defend against oxidative stress induced by hyperglycemia, and the antioxidant enzyme activity is abnormally increased, and the balance maintained between these enzymes is broken.

In one embodiment of the present invention, it was confirmed that the compounds of Formula 1 described above (in particular, the most preferred example is a compound of Formula 1-1 or Formula 1-2) can alleviate oxidative stress caused by diabetes and high blood sugar. That is, the compounds exhibited the effect of promoting blood glucose absorption into hepatocytes, and it was confirmed that there is an effect of suppressing the generation of reactive oxygen species (ROS) and removing ROS due to endoplasmic reticulum stress.

Meanwhile, in the present invention, the term 'fatty liver disease' may refer to a group of diseases encompassing all aspects of the disease from fatty liver to steatohepatitis to fatty liver-associated cirrhosis.

The above-mentioned 'fatty liver' is caused by the accumulation of fat in the liver due to excessive fat or alcohol intake, increased fat synthesis in the liver, excretion of triglycerides, and decreased burning, in general, fatty liver is defined when the proportion of fat accumulated in the liver is more than 5%. Most of the fat accumulated in the fatty liver is triglycerides.

Fatty liver can be divided into alcoholic fat caused by excessive drinking and non-alcoholic fatty liver caused by liver and obesity, diabetes, hyperlipidemia, or drugs. Alcoholic fatty liver occurs because excessive alcohol intake promotes fat synthesis in the liver and prevents normal energy metabolism. On the other hand, nonalcoholic fatty liver occurs more frequently in people suffering from obesity, insulin intolerance, and diabetes. This phenomenon suggests that nonalcoholic fatty liver may be caused by an increase in the concentration of free fatty acids in the blood due to insulin resistance or excessive lipolysis (ABMayerson et al., Diabetes, 51: 797-802 (2002); K F Petersen et al., Diabetes, 54:603-608 (2005)).

In the present invention, the fatty liver may be any one or more selected from the group consisting of alcoholic fatty liver, non-alcoholic fatty liver, nutritive fatty liver, starvation fatty liver, obese fatty liver, and diabetic fatty liver, preferably, it may be non-alcoholic fatty liver, obese fatty liver, or diabetic fatty liver, and most preferably, it may be diabetic fatty liver, but is not limited thereto.

In the present invention, the term 'steatohepatitis' refers to a case of inflammatory findings or fibrotic lesions accompanied by hepatocyte damage (balloon degeneration) while showing fat deposition in the liver. It is used to distinguish it from 'fatty liver', which is a case in which fat deposition in the liver is shown but liver cell damage (balloon degeneration) and fibrosis are not found.

In the present invention, the term 'fatty liver-associated cirrhosis' refers to liver cirrhosis accompanied by histological findings of fatty liver or steatohepatitis, or cirrhosis occurring in a patient with fatty liver or steatohepatitis histologically proven in the past.

In one preferred embodiment (embodiment), fatty liver disease of the present invention means 'non-alcoholic fatty liver disease'. The non-alcoholic fatty liver disease is meant to include non-alcoholic fatty liver, non-alcoholic steatohepatitis, and non-alcoholic fatty liver-associated cirrhosis, and if it is known in the art as the disease group, the type is not limited thereto.

According to an embodiment of the present invention, it was confirmed that the above-described compounds (in particular, the most preferred example is a compound of Formula 1-1 or Formula 1-2) exhibit an effect of inhibiting the accumulation of fat in liver cells, thereby exhibiting a preventive or therapeutic effect of fatty liver. In addition, it was confirmed that the therapeutic effect of steatohepatitis was remarkable.

The composition provided in the present invention is not limited thereto, but may preferably be a food composition or a pharmaceutical composition.

In the food composition according to the present invention, the above-mentioned compounds (in particular, the most preferred example is a compound of Formula 1-1 or Formula 1-2) or pharmaceutically acceptable salts thereof may be provided in the form (type) of various food compositions such as functional food, nutritional supplement, health food and food additives.

Food compositions of this type can be prepared in various forms according to conventional methods known in the art. Although not limited thereto, for example, as a health food, the compound is prepared (added) in the form of tea, juice, and drink and provided in a liquefied manner so that it can be consumed, or it can be provided by granulation, encapsulation and powdering.

For example, food is not limited to, but it can prepared by adding the compound to beverages (including tea, juices and drinks, and alcoholic beverages), fruits and their processed foods (e.g., canned fruit, canned fruit, jam, marmalade, etc.), fish, meat and their processing Food (e.g., ham, sausage corned beef, etc.), breads and noodles (e.g., udon, soba, ramen, spaghetti, macaroni, etc.), fruit juice, various drinks, cookies, syrup, dairy products (e.g., butter, cheese, etc.), edible vegetable oils and fats, margarine, vegetable protein, retort food, frozen food, various seasonings (e.g., soybean paste, soy sauce, sauce, etc.).

In addition, in the pharmaceutical composition according to the present invention, the above-mentioned compounds (in particular, the most preferred example is a compound of Formula 1-1 or Formula 1-2) or pharmaceutically acceptable salts thereof may be administered in various oral and parenteral formulations during clinical administration. In the case of formulation, it can be prepared using commonly used diluents or excipients such as fillers, extenders, binders, wetting agents, disintegrants, and surfactants.

Solid preparations for oral administration include tablets, patients, powders, granules, capsules, troches, etc., such a solid preparation may be prepared by mixing one or more compounds of Formula 1 or a pharmaceutically acceptable salt thereof of the present invention with at least one excipient, for example, starch, calcium carbonate, sucrose or lactose or gelatin etc. In addition to simple excipients, lubricants such as magnesium stearate, talc and the like may also be used. Liquid formulations for oral administration include suspensions, oral solutions, emulsions, or syrup, in addition to water and liquid paraffin, which are commonly used simple diluents, various excipients, for example, wetting agents, sweetening agents, fragrances, preservatives, and the like may be included.

Agents for parenteral administration include sterile aqueous solutions, non-aqueous solutions, suspension solutions, emulsions, lyophilized formulations, and suppositories. Non-aqueous solvents and suspensions may include propylene glycol, polyethylene glycol, vegetable oils such as olive oil, and injectable esters such as ethyl oleate. As the base of the suppository, witepsol, macrogol, tween 61, cacao butter, laurin fat, glycerol, gelatin, etc. may be used.

In addition, the dosage for the human body of the above-mentioned compounds (in particular, the most preferred example is a compound of Formula 1-1 or Formula 1-2) or a pharmaceutically acceptable salt thereof may vary depending on the patient's age, weight, sex, dosage form, health status and disease degree, based on an adult patient weighing 70 kg, it is generally 0.01 to 1000 mg/day (day), preferably 0.1 to 500 mg/day (day), in addition, according to the judgment of the doctor or pharmacist, divided administration may be administered once or several times a day at regular time intervals.

The pharmaceutical composition of the present invention may be used alone or in combination with methods using surgery, hormone therapy, chemotherapy, and biological response modifiers.

On the other hand, the compound according to the present invention can be formulated in various forms depending on the purpose. Agent examples for the composition of the present invention are exemplified below.

Agent Example 1: Preparation of a Pharmaceutical Agent

1. Preparation of Powder
   a compound of formula 1 according to the present invention 2 g
   lactose 1 g
   The above ingredients were mixed and filled in an airtight cloth to prepare a powder.
2. Preparation of Tablets
   the compound of formula 1 according to the present invention 100 mg
   Corn Starch 100 mg
   Lactose 100 mg
   Magnesium stearate 2 mg
   After mixing the above ingredients, tablets were prepared by tableting according to a conventional method for manufacturing tablets.
3. Preparation of Capsules
   the compound of formula 1 according to the present invention 100 mg
   Corn Starch 100 mg
   Lactose 100 mg
   Magnesium stearate 2 mg
   After mixing the above ingredients, the capsules were prepared by filling in gelatin capsules according to a conventional manufacturing method of capsules.
4. Preparation of Pills
   the compound of formula 1 according to the present invention 1 g
   lactose 1.5 g
   glycerin 1 g
   xylitol 0.5 g
   After mixing the above components, it was prepared so as to be 4 g per pill according to a conventional method.
5. Preparation of Granules
   the compound of formula 1 according to the present invention 150 mg
   Soybean extract 50 mg
   glucose 200 mg
   Starch 600 mg
   After mixing the above components, 100 mg of 30% ethanol was added and dried at 60° C. to form granules, and then filled in a bag.

In addition, the present invention provides the use of the compound of Formula 1 or a pharmaceutically acceptable salt thereof for preparing an agent for the prevention or treatment of metabolic diseases.

<Formula 1>

Wherein R1, R2, R3, R4, R5 and R6 are each independently selected from the group consisting of hydrogen, halo, hydroxy, amino, carboxyl, cyano, nitro, alkyl, alkenyl, alkynyl and alkoxy.

In addition, the present invention provides the method of treating a metabolic disease comprising administering to a subject in need thereof an effective amount of a composition comprising the compound of Formula 1 or a pharmaceutically acceptable salt thereof as an active ingredient <Formula 1>

Wherein R1, R2, R3, R4, R5 and R6 are each independently selected from the group consisting of hydrogen, halo, hydroxy, amino, carboxyl, cyano, nitro, alkyl, alkenyl, alkynyl and alkoxy.

The 'effective amount' of the present invention refers to an amount that, when administered to an individual, exhibits an effect of improving, treating, preventing, detecting, diagnosing, or inhibiting or reducing a metabolic disease. The 'subject' may be an animal, preferably an animal, including a mammal, particularly a human, and may be a cell, tissue, organ, or the like derived from an animal. The subject may be a patient in need of the effect.

The 'treatment' of the present invention refers to improving a metabolic disease or symptom of a metabolic disease comprehensively, which may include curing, substantially preventing, or improving the condition of a metabolic disease, including, but not limited to, alleviating, curing or preventing one or most symptoms resulting from a metabolic disease.

In the present invention, the term 'comprising' is used synonymously with 'comprising' or 'characterized', and in the composition or method, additional component elements or method steps not mentioned are not excluded. The term 'consisting of' means excluding additional elements, steps, or ingredients not otherwise specified. The term 'essentially consisting of' means, in the scope of the composition or method, including the described component elements or steps as well as the component elements or steps that do not substantially affect the basic properties thereof.

Advantageous Effect

The compound disclosed in the present invention has a remarkable CYP4A inhibitory effect and promotes glucose uptake into hepatocytes, inhibits fat accumulation in liver cells, inhibits free radicals caused by endoplasmic reticulum stress, exhibits activity such as steatohepatitis treatment, so it can be very usefully used in the development of therapeutics for metabolic diseases such as diabetes and fatty liver disease. In addition, the compounds have a significant inhibitory effect on CYP4A, and have a simultaneous therapeutic effect on various CYP4A-related diseases, particularly CYP4A overexpression diseases.

BRIEF DESCRIPTION OF THE DRAWINGS

Specifically, after mixing each test compound, CYP4A expressing cell lysate, and Luciferin-4A, and allowing the CYP4A reaction to occur sufficiently, the ability of each compound to inhibit CYP4A activity was measured by comparing the luminescence value of the cells (N/C: control group using wild-type HepG2 cell lysate, Cyp4a11: group reacted only with CYP4A expressing cell lysate without compound treatment, HET0016: group treated with CYP4A expressing cell lysate with HET0016 compound, Candi #18 and Candi #18-1: group treated with the compound of Formula 1-1 in CYP4A expressing cell lysate, Candi #18-2: group treated with the compound of Formula 1-2 in CYP4A expressing cell lysate).

MODE FOR CARRYING OUT INVENTION

Hereinafter, the present invention will be described in detail.

However, the following examples are only illustrative of the present invention, and the content of the present invention is not limited to the following examples.

Example 1: Selection of Compounds Exhibiting CYP4A Inhibitory Activity

The present inventors selected CYP4A inhibitors through screening of a commercially available compound library based on the content of the prior invention that compounds exhibiting CYP4A inhibitory activity can exhibit preventive or therapeutic effects for diabetes and fatty liver.

CYP4A11 DNA (GenBank: S67580.1) was transfected into HepG2 cells, a human liver cell line, and cultured in an incubator for 24 hours so that the protein was expressed. After that, cells were pulverized by adding RIPA buffer (20 mM Tris-HCl (pH 7.5), 150 mM NaCl, 1 mM $Na_2$EDTA, 1 mM EGTA, 1% NP-40, 1% sodium deoxycholate, 2.5 mM sodium pyrophosphate, 1 mM b-glycerophosphate, 1 mM $Na_3VO_4$, 1 μg/ml leupeptin) to extract proteins, and then CYP4A activity experiment and compound screening were performed as follows.

First, each candidate compound was mixed with water by concentration in a 96-well plate (white opaque polystyrene nontreated flat-bottom well) (in the experiment of FIG. 1, all compounds were used at 5 μM), then 1M KPO4 buffer (13.94 g $K_2HPO_4$, 2.72 g $KH_2PO_4$, based on 100 ml), 5 mM Luciferin-4A, and 1 pmol CYP4A expressing cell (HepG2) lysate were added and reacted at room temperature for 10 minutes.

After putting it in the NADPH Regeneration system (20× sol.A, 100× sol.B in water, Cal. Number: D399, Thermo Fisher SCIENTIFIC), leave it at room temperature for 1 hour to allow the CYP4A reaction to occur sufficiently, and CYP4A reaction is finished by adding Luciferin Detection reagent, and induce a luminescence reaction to occur, and the reaction was carried out at room temperature for 20 minutes. The degree of inhibition of CYP4A activity was measured by comparing the luminescence values from each well with a microplate reader.

Figure 1:
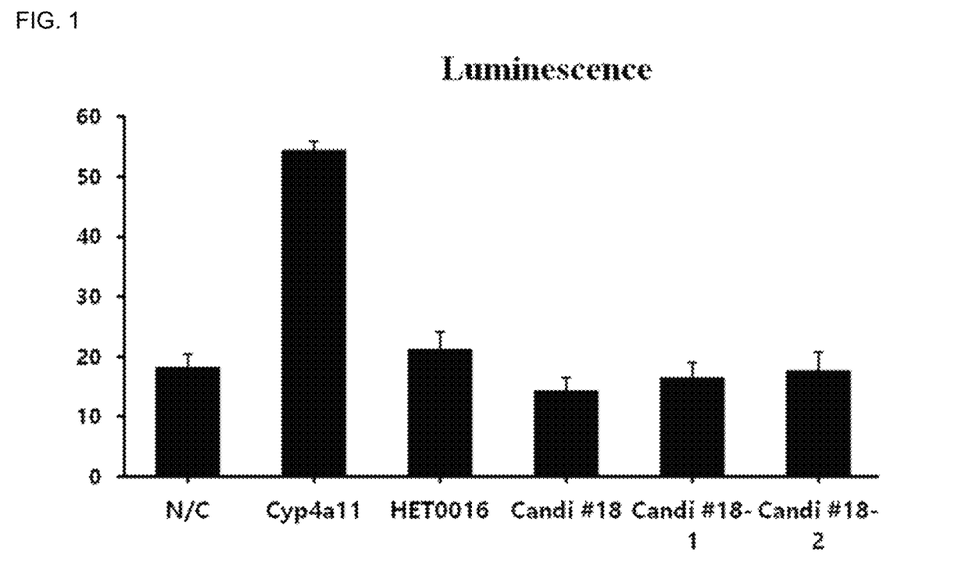
FIG. 1 shows the results of measuring the degree of inhibition of CYP4A activity by treating the compound of Formula 1.
Figure 2:
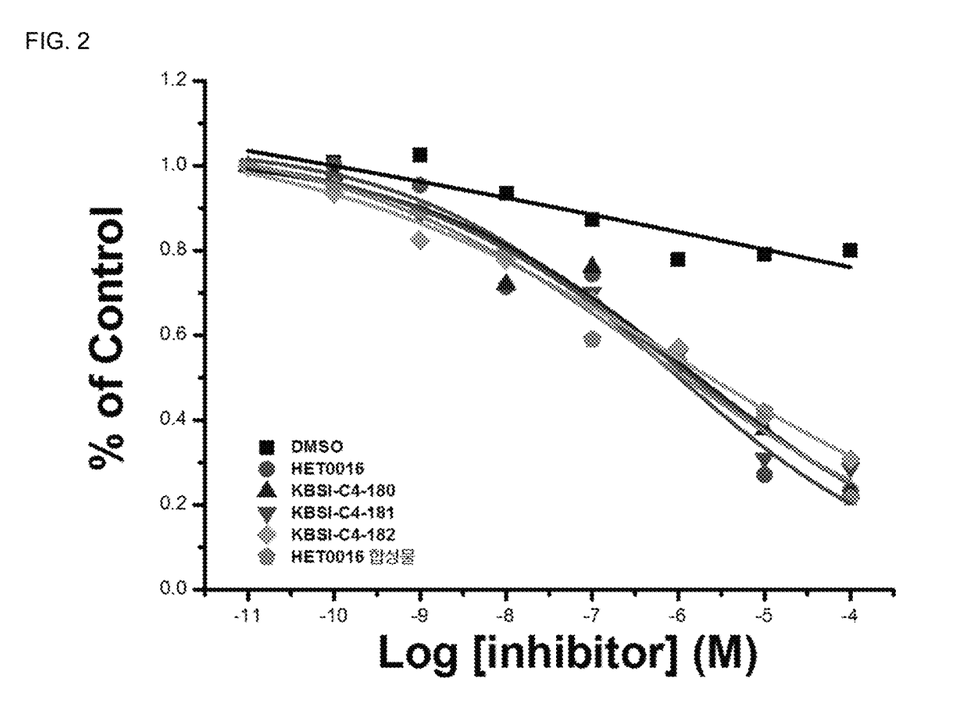
FIG. 2 is a result of measuring the CYP4A activity inhibition ability according to the concentration of the test compounds as a luminescence value (DMSO (square): treatment with dimethyl sulfoxide, HET0016 (circle): HET0016 compound is purchased and treated commercially, KBSI-C4-180 (forward triangle) and KBSI-C4-181 (reverse triangle): treatment with the compound of Formula 1-1, KBSI-C4-182 (rhombus): treatment with the compound of Formula 1-2, HET0016 compound (pentagon): treatment with HET0016 compound synthesized in the laboratory).

As a result, it was confirmed that the compounds having the structure of Formula 1 provided in the present invention had remarkable inhibitory ability of CYP4A, and they were selected. FIG. 1 and FIG. 2 representatively show the effects of compound #18-1 (compound of formula 1-1) and compound #18-2 (compound of formula 1-2), which were particularly excellent among the selected compounds.

It was confirmed that the compounds having the structure of Formula 1 exhibited better CYP4A inhibitory ability than HET0016 (N-hydroxy-N'-(4-butyl-2-methylphenyl)-formamidine), a known CYP4A-specific inhibitor, and the IC50 value was similar to HET0016.

Example 2: Glucose Absorption Promoting Effect

HepG2 cells, a human liver cell line, were cultured in a high-glucose DMEM (Dulbecco's modified Eagle's medium, glucose 25 mM) medium in the presence of 10% fetal bovine serum (FBS), and then glucose uptake experiments were performed as follows.

First, HepG2 cells were grown to $1×10^4$ cells/well in a 96-well plate (black, clear bottom culture plate) by the above method, and then 5 μM of each compound screened in Example 1 was added and incubated for 6 hours. Here, thapsigargin or tunicamycin, which induces endoplasmic reticulum stress, was added to hepatocytes, and then placed in an incubator at 37° C. for 24 hours to react. After that, insulin and 2-NBDG (2-(N-(7-Nitrobenz-2-oxa-1,3-diazol-4-yl)Amino)-2-Deoxyglucose) were added and reacted in an incubator at 37° C. for 3 hours, and after washing with PBS (phosphate buffered saline), fluorescence was measured with a microplate reader (Excitation: 488 nm, Emission: 508 nm).

Figure 3A:
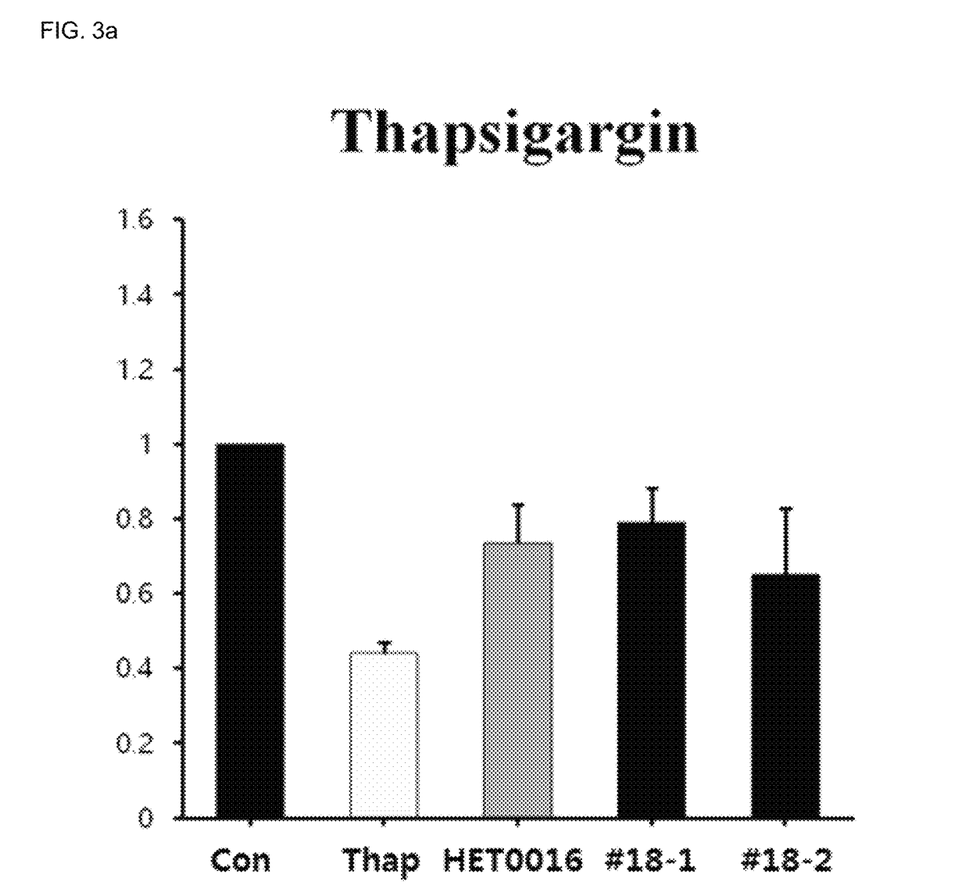
FIG. 3A and FIG. 3B show the results of confirming the glucose absorption promoting effect of the test compounds by fluorescence. Specifically, after reacting Thapsigargin or Tunicamycin inducing ER stress to hepatocytes cultured with each test compound, insulin and 2-NBDG were reacted to confirm the glucose absorption promoting effect of the compounds of the present invention (Excitation: 488 nm, Emission: 508 nm).
Figure 3B:
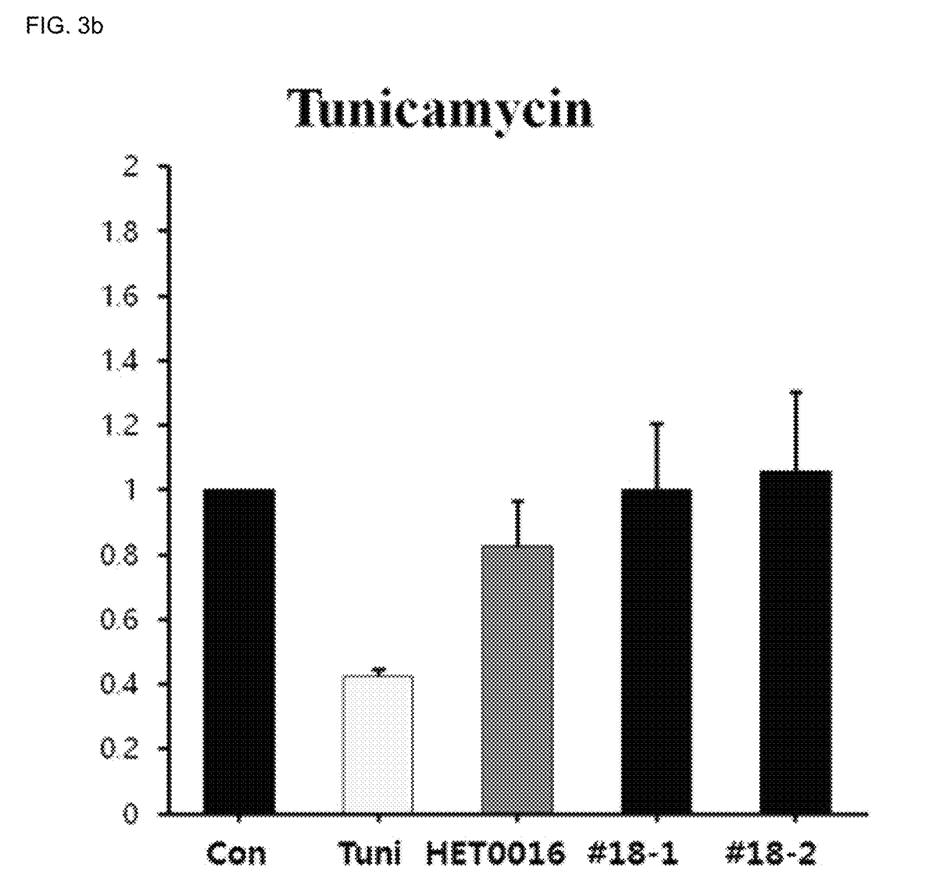

As a result, the control group treated only with Thapsigargin or Tunicamycin without the test substance treatment significantly inhibited glucose uptake compared to the control group. On the other hand, as representatively shown in FIG. 3a and FIG. 3b, in the test group treated with the compound #18-1 (Compound of Formula 1-1) or #18-2 (Compound of Formula 1-2), it was confirmed that the glucose absorption promoting effect was significant to the same or higher degree than that of the positive control group (HET0016). In particular, as seen in the Tunicamycin-treated group the compound #18-1 (Compound of Formula 1-1) or #18-2 (Compound of Formula 1-2) was more effective in promoting glucose absorption than the known HET0016 compound.

Example 3: Fat Accumulation Inhibitory Activity in Hepatocytes

After culturing HepG2 cells, a human liver cell line, in a high-concentration DMEM medium (Dulbecco's modified Eagle's medium, glucose 25 mM) containing 10% fetal bovine serum (FBS), an experiment was performed to measure fat accumulation by the following method.

First, HepG2 cells were grown to $5×10^3$ cells/well in a 96-well plate (black, clear bottom culture plate) by the above method, and 5 μM of each compound screened in Example 1 was added thereto, followed by incubation for 6 hours. Here, palmitate, a fatty acid that induces fat accumulation in hepatocytes, is added, and then placed in an incubator at 37° C. for 72 hours to react. Thereafter, 4% paraformaldehyde was added and reacted at room temperature for 15 minutes to fix, and then Nile-Red solution was added, light was blocked, and reaction was performed at 37° C. for 10 minutes. After the reaction time, fluorescence was measured with a microplate reader (Excitation: 530 nm, Emission: 635 nm).

Figure 4:
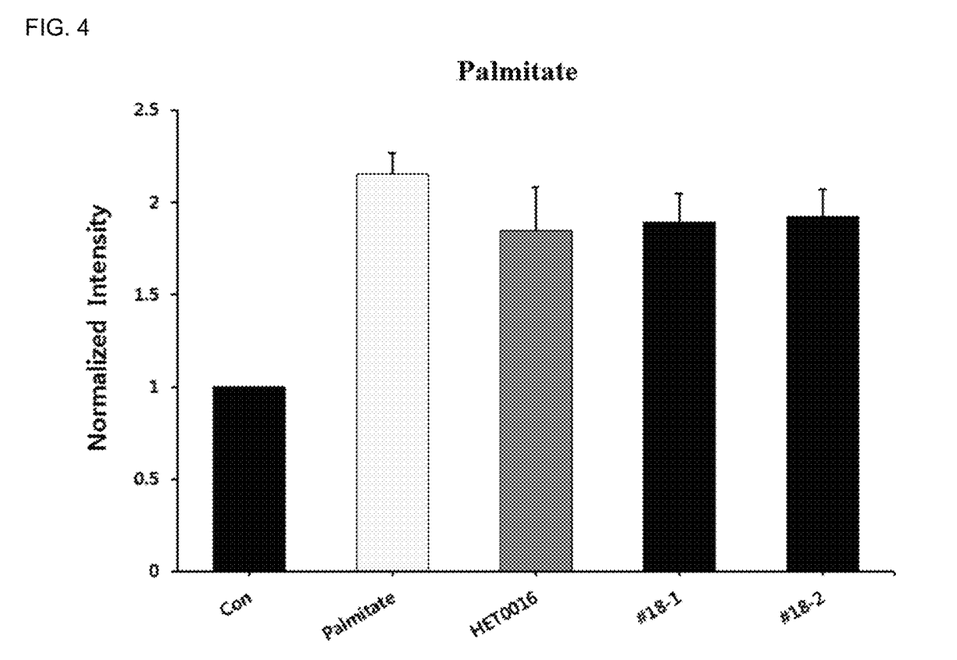
FIG. 4 is a result showing the fat accumulation inhibitory activity in hepatocytes of the test compounds. Specifically, after reacting each test compound with palmitate, a fatty acid that induces fat accumulation, in cultured hepatocytes, the difference in the degree of fat accumulation was quantified using fluorescence (Excitation: 530 nm, Emission: 635 nm).

As a result, it was confirmed that a large amount of fat was accumulated in the control cells to which palmitate was reacted without treatment with the test substance compared to the control group. On the other hand, as representatively shown in FIG. 4, in the test group treated with the compound #18-1 (Compound of Formula 1-1) or the compound #18-2 (Compound of Formula 1-2), fat accumulation in liver cells was suppressed to a degree similar to that of the positive control group (HET0016).

Example 4: Active Oxygen Scavenging Ability

After culturing HepG2 cells, a human liver cell line, in high-glucose DMEM medium (Dulbecco's modified Eagle's medium, glucose 25 mM) in the presence of 10% fetal bovine serum (FBS), an experiment was performed to measure the ability to remove reactive oxygen species by the following method.

First, HepG2 cells were grown to $1×10^4$ cells/well in a 96-well plate (black, clear bottom culture plate) by the above method, and then 5 μM of each compound screened in Example 1 was added and incubated for 6 hours. After adding thapsigargin or tunicamycin to induce endoplasmic reticulum stress, the reaction was put in an incubator for 24 hours. After that, 5 μM H2DCFDA (cell-permeant 2',7'-dichlorodihydrofluorescein diacetate) was added and reacted for 30 minutes in an incubator at 37° C. Thereafter, after washing with PBS, it was placed in an incubator at 37° C. for 30 minutes and waited for luminescence to occur. Thereafter, fluorescence was measured with a microplate reader (Excitation: 488 nm, Emission: 508 nm).

Figure 5A:
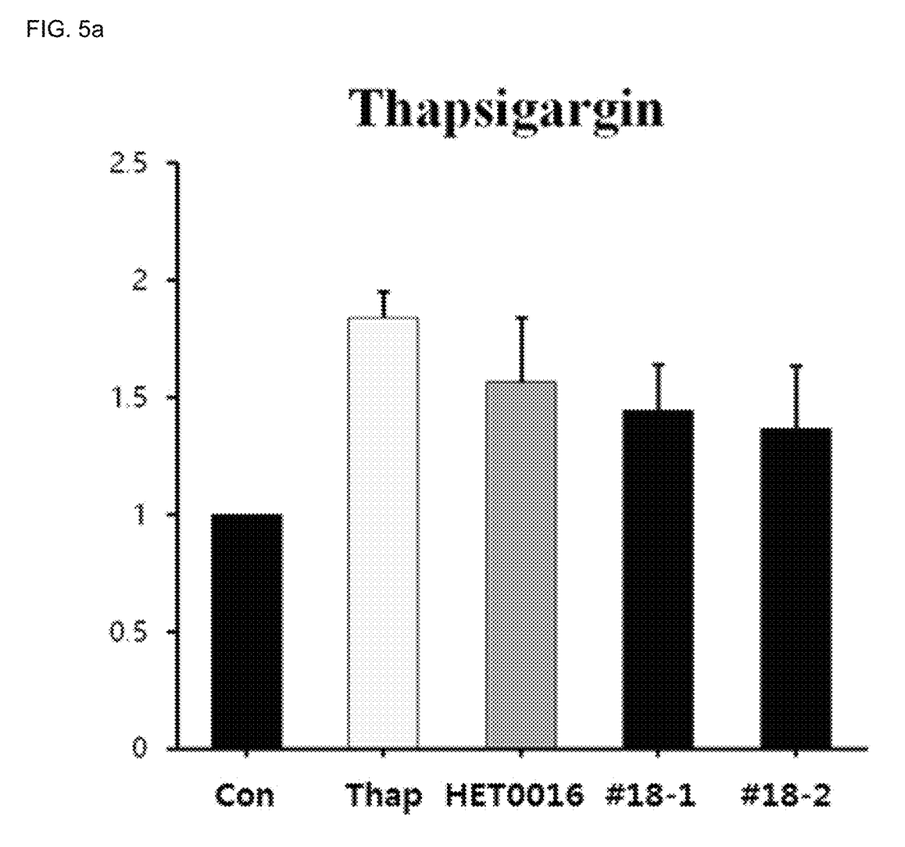
FIG. 5a and FIG. 5b are results showing the active oxygen scavenging ability of the test compounds. Specifically, after reacting each test compound with Thapsigargin or Tunicamycin, which induces ER stress, in cultured the hepatocytes, the difference in the amount of ROS (reactive oxygen species) was quantified using luminescence (Excitation: 488 nm, Emission: 508 nm).
Figure 5B:
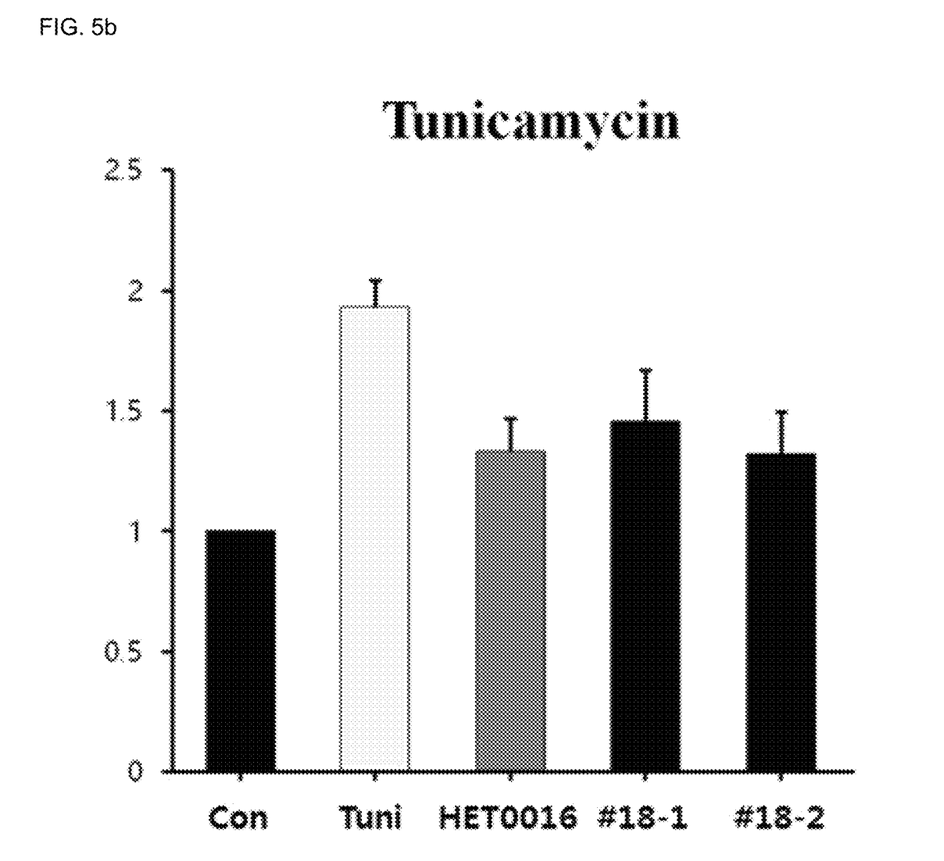

As a result, it was confirmed that the amount of ROS was rapidly increased in the control group treated only with Thapsigargin or Tunicamycin without treatment with the test substance compared to the control group. On the other hand, as representatively shown in FIG. 5a and FIG. 5b, it was confirmed that the amount of ROS was significantly decreased in the test group treated with the compound #18-1 (Compound of Formula 1-1) or the compound #18-2 (Compound of Formula 1-2), and this effect was equal to or greater than that of the positive control group (HET0016). In particular, in the Thapsigargin-treated group, both #18-1 and #18-2 showed better inhibition of ROS production and removal of ROS than HET0016. Free radicals are also associated with inflammatory conditions. In fact, the effects of #18-1 and #18-2 compounds on steatohepatitis were demonstrated in subsequent experiments.

INDUSTRIAL APPLICABILITY

The compound disclosed in the present invention has a remarkable CYP4A inhibitory effect, and exhibits activities such as promoting glucose absorption into hepatocytes, inhibiting fat accumulation in hepatocytes, inhibiting reactive oxygen species caused by ER stress, and treating steatohepatitis. Since it can be very usefully used in the development of therapeutics for metabolic diseases for diabetes and fatty liver disease, it has excellent industrial applicability. In addition, since the compounds have a significant inhibitory effect on CYP4A, and have a simultaneous therapeutic effect on various CYP4A-related diseases, particularly CYP4A overexpression diseases, it has great industrial applicability in fields such as the pharmaceutical industry.

What is claimed is:

1. A method of treating a diabetes and fatty liver disease comprising administering to a subject a pharmaceutically effective amount of a pharmaceutical composition comprising the compound of Formula 1 or a pharmaceutically acceptable salt thereof as an active ingredient:

<Formula 1> wherein R1, R2, R3, R4, R5 and R6 are each independently selected from the group consisting of hydrogen, halo, hydroxy, amino, carboxyl, cyano, nitro, alkyl, alkenyl, alkynyl and alkoxy.

2. The method according to claim 1, wherein the alkyl is C1-C6 linear or branched alkyl, the alkenyl is C1-C6 linear or branched alkenyl, the alkynyl is C1-C6 linear or branched alkynyl, and the alkoxy is C1-C6 linear or branched alkoxy.

3. The method according to claim 1, wherein R1, R2, R4, R5 and R6 in the compound are hydrogen, and wherein R3 is selected from the group consisting of halo, hydroxy, amino, carboxyl, cyano, nitro, C1-C6 linear or branched alkyl, C1-C6 linear or branched alkenyl, C1-C6 linear or branched alkynyl, and C1-C6 linear or branched alkoxy.

4. The method according to claim 1, wherein R1, R2, R4, R5 and R6 in the compound are hydrogen, and wherein R5 is selected from the group consisting of halo, hydroxy, amino, carboxyl, cyano, nitro, C1-C6 linear or branched alkyl, C1-C6 linear or branched alkenyl, C1-C6 linear or branched alkynyl, and C1-C6 linear or branched alkoxy.

5. The method according to claim 1, wherein the compound is N-(4-((4-(7-chloroquinolin-4-yl) piperazin-1-yl) sulfonyl) phenyl) acetamide; or N-(4-((4-(2-methylquinolin-4-yl) piperazin-1-yl) sulfonyl) phenyl) acetamide.

6. The method according to claim 1, wherein the diabetes is type 2 diabetes.

7. The method according to claim 1, wherein the diabetes is derived from obesity.

8. The method according to claim 1, wherein the fatty liver disease is fatty liver, steatohepatitis, and/or fatty liver-associated cirrhosis.

* * * * *